United States Patent [19]

Salinas

[11] Patent Number: 5,665,342
[45] Date of Patent: Sep. 9, 1997

[54] SCALP AND HAIR CARE PRODUCT AND PROCESS OF PREPARING SAME

[76] Inventor: Ofelia Salinas, Rte. 2, Box 685, Bishop, Tex. 78343

[21] Appl. No.: 470,011

[22] Filed: Jun. 6, 1995

[51] Int. Cl.$^6$ .............................. A61K 7/06; A61K 35/78
[52] U.S. Cl. .......................... 424/74; 424/195.1; 514/880
[58] Field of Search ................ 424/401, 195.1, 424/74; 514/880

[56] References Cited

U.S. PATENT DOCUMENTS

| | | | |
|---|---|---|---|
| Re. 33,993 | 7/1992 | Grollier et al. | 424/74 |
| 4,933,177 | 6/1990 | Grollier et al. | 424/74 |
| 5,000,949 | 3/1991 | Bias | 424/74 |
| 5,152,990 | 10/1992 | Miyauchi | 424/400 |
| 5,157,036 | 10/1992 | Grollier | 514/256 |
| 5,217,711 | 6/1993 | DeOliveira | 424/70 |
| 5,288,485 | 2/1994 | Kikuta et al. | 424/74 |

FOREIGN PATENT DOCUMENTS

| | | |
|---|---|---|
| 149120 | 8/1937 | Austria . |
| 1485641 | 3/1967 | France . |
| 46074 | 5/1928 | Norway . |
| 179254 | 12/1935 | Switzerland . |
| 399007 | 7/1933 | United Kingdom . |

*Primary Examiner*—Edward J. Webman
*Attorney, Agent, or Firm*—Daniel Vera

[57] ABSTRACT

A live hair and skin treating cosmetic formulation containing a mixture of biochemicals obtained by boiling in water a composition containing potato peelings and lantana leaves.

19 Claims, No Drawings

SCALP AND HAIR CARE PRODUCT AND PROCESS OF PREPARING SAME

FIELD OF THE INVENTION

This invention relates to a composition for treating human scalp and hair and particularly relates to a process for growth of human hair.

BACKGROUND OF THE INVENTION

The cosmetic and pharmaceutical industries are constantly searching for new and useful compositions for treating ubiquitous problems such as baldness, dry skin, dandruff, sunburn and the like. Remedies for these conditions have been somewhat successful at best. There is a definite need for more advanced treatments, especially in the area of male pattern baldness.

Man has a stock of about 90,000 to 140,000 hairs on his scalp. It is normal for him to lose about 50 to about 80 hairs per day. Hair depends on the papilla for it's growth. As long as the papilla is not destroyed, the hair will normally grow back. In humans, new hair replaces old hair in the following manner: the bulb loosens and separate from the papilla; the bulb then moves slowly to the surface, as hair grow by cell division which takes place at the root of the hair around the papilla.

Hair growth is influenced by season of the year, nutrition, hormones and the like. Cold air will cause the hair to contract. Heat will cause the hair to expand and more readily absorb moisture. The natural shedding of hair occurs more rapidly in the spring and fall.

The condition known as alopecia refers to hair loss which does not return. Alopecia senilis is the form of baldness occurring in old age. Alopecia prematura is the form of baldness occurring in early to middle age. Both conditions begin with a slow thinning process which is caused by strong hairs falling out and being replaced by weaker ones.

U.S. Patent No. 4,933,177 to Grollier et al. discloses a cosmetic composition for treating the hair and skin comprising powders of pulverized plant substances. Roots, stems, leaves, flowers, fruits and seeds can be employed. Many varieties of plants are disclosed such as acacia, witch hazel, tormentil, dog rose and rhatany.

U.S. Pat. No. Re 33,993 to Grollier et al. relates to a cosmetic composition for treatment of the hair and skin comprising, in an aqueous medium, particles of pulverized flowers or flower tops. Many varieties of plants, shrubs and trees are disclosed as possible sources for flowers or flower tops. Some of these are: wormwood, acacia, yarrow, columbine, mugwort, honeysuckle, crocus, oleander, apple tree, sage and the like.

U.S. Pat. No. 5,288,485 to Kukuta et al. discloses a hair growth promoting agent comprising an extract of the plant hypericum erectum thumb, a Chinese medicinal herb. Extraction is performed with an organic solvent. Leaf, stem, root, fruit, seed or flower can be utilized.

U.S. Pat. No. 5,000,949 to Bias teaches the use of a hair growth composition comprising petroleum jelly, an oil extract of cactus, glycerin and oil of clover. In the preparation, cactus leaves and other solids are removed as by filtration and straining.

The present invention relates to a method for preparing an aqueous composition which enables the effects of alopecia to be eliminated or reduced, and in particular enable hair growth to be induced or stimulated or its loss decreased. The composition also exhibits benefits advantageous to the human skin such as relief from dryness and the like.

SUMMARY OF THE INVENTION

Both the pharmaceutical and the cosmetic industry have employed numerous formulations containing active substances derived from plants by extractive processes. In certain cases, the active substances are obtained from the specified plants by pulverization followed by extraction with organic solvent.

The present invention relates to a cosmetic composition for treatment of the skin and hair comprising both active substances and inactive substances. They are obtained by a process comprising the steps of obtaining an amount of water, adding to the water a mixture of potato skins and lantana leaves, heating the mixture to boiling, maintaining the boiling of the water for a time of about three minutes to about one hour, typically from about 3 to about 30 minutes, e.g.; about 20 minutes, allowing the mixture to cool to ambient temperature, and filtering the cooled mixture to obtain an aqueous solution of biochemicals. The biochemicals contain both active and inactive substances.

Typically, the aqueous solution would be prepared from about 200 to 300 ml. water, e.g., 240 ml., from about 1 to about 50 gm. of potato skins, e.g., 3 peelings about each 8 centimeters in length, and from about 0.3 to about 5 gm. of lantana leaves, e.g., 7 to 8 lantana leaves. In a preferred embodiment, the aqueous solution of biochemicals is recovered as filtrate and placed under conditions of refrigeration.

The present invention also relates to a method of using the disclosed composition for treating alopecia, dryness of skin and the like in human subjects.

DETAILED DESCRIPTION OF THE INVENTION

Lantana Camara L. is of the family VERBENACEAE and is commonly known as lantana. It is native to tropical countries such as Venezuela, the Bahamas, Surinam, Hawaii, Panama, Mexico, Costa Rica, Jamaica, El Salvador, Southern China, Indonesia, Australia and Malaysia. In the United States, the plant is found in sandy coastal plain soils in Florida and Texas.

The lantana plant contains lantanine, a triterpenoid, and other compounds irritating to the mucosa of the gastrointestinal tract. All parts of the plant are very toxic. Children have been poisoned by eating the berries.

Historically, the plants have been used in folk remedies for diverse diseases such as cancer, malaria, leprosy, measles, mumps, jaundice, asthma, dysentery, consumption, hemorrhage, yellow fever, rheumatism, venereal diseases and the like.

The leaves of the lantana plant contain, as well as lantanine (0.2–0.7% by weight), lantadene B (0.2% by weight), icterogenic, essential oil with citral and other sesquiterpenes (0.05% to 0.2% by weight), caryophyllene (up to 80% by weight), phellandrene (10% to 12% by weight), dipentene, terpineol, geraniol, linalool, cineole, eugenol, furfural, tannins, resins, dyestuffs, reduced sugars, lantadene methyl-3-oxo-ursolate (17% by weight), lantanol acid and lantanic acid. Lantanine is known to depress circulation and lower body temperature.

The skin of the potato contains vitamin D, minerals and other organic matter.

The present invention relates to a cosmetic composition containing hydrophilic biochemicals contained in lantana leaves and potato skins. The composition is easily prepared and is stable for a number of days when properly refrigerated.

The invention further relates to a method of treating the hair and scalp of a human. The method comprises the steps of administering to the hair and scalp of an individual a small mount, typically from about ½ to about 1 ounce, of a hair growth promoting composition comprising an effective mount of the cosmetic composition which contains hydrophilic biochemicals extracted from the leaves of the lantana plant and the skins of potatoes, massaging the hair and scalp of the individual and leaving the composition on the scalp and hair for an extended period of time, e.g., the composition is not rinsed off for at least about four to eight hours. In a preferred embodiment, the administration of the cosmetic composition is repeated more than once a day, e.g., at least two or three times a day.

The following examples are included as illustrative of the present invention, but are in no way meant to limit the inventive concept, except as limited by what is explicitly recited in the claims.

EXAMPLE 1

Three potato peelings having a length of about eight centimeters are obtained. The peelings, which weigh approximately 4 gms., are added to a metal cooking pot along with seven or eight lantana leaves (approximately 1 gm) and about 250 milliliters of water. The pot is then covered with a lid having an outlet for steam. Heat is applied to the cooking pot until the water begins to boil. The heat is then reduced, the lid is removed, and the mixture of leaves and peelings is boiled at a controlled rate for a period of about three to five minutes. Heat is removed and the aqueous solution containing water soluble biochemicals is strained through three layers of cheesecloth to remove leaves and other solid materials. The solution is poured while hot into suitable jars or containers. The jars can be sealed and placed in boiling water bath for a period of about twenty minutes. Jars are then removed from the bath and cooled.

EXAMPLE 2

A 47 year old man having a medical history of high blood pressure and taking medication for that condition was treated three times a day with about 1 ounce per treatment of the cosmetic composition of the present invention as prepared in Example 1. The man has thinning hair on the top of his scalp. The treatment was continued on a daily basis for ten days. Positive results were observed after ten days. No side effects were reported.

EXAMPLE 3

A 51 year old man who had lost his hair at age 31 was treated with the hair growth formula as prepared in Example 1. Results began to appear after three weeks; and after eight weeks hair growth was most obvious. No side effects were reported.

EXAMPLE 4

A 35 year old man with a medical history of high blood pressure and on medication was treated with the hair growth formula of Example 1. The formula was used twice daily. Results were seen in four weeks: new hair growth on top of the head. No side effects were reported.

EXAMPLE 5

A 36 year old man having a medical history of kidney stones was treated with the hair growth formulation of the present invention. The man has a mustache which is not full. The treatment was continued on a daily basis for eight days. After 8 days the mustache began to look thicker. No side effects were reported as a result of using this formulation.

EXAMPLE 6

A 48 year old woman having a medical history of pancreatic problems and taking insulin was treated with the hair growth formulation of the present invention. The treatment was administered twice daily for a period of three months. New hair growth was observed. No side effects were reported as a result of using the formulation.

EXAMPLE 7

A 59 year old man having no prior major medical problems and under no medication was treated with hair growth formula of the present invention. The man had been bald for more than 20 years. After 60 days, new hair growth was visually observed. No side effects were reported as a result of using the formulation.

EXAMPLE 8

A 62 year old man having a medical history of prostate problems was treated with the hair growth formulation of the present invention. The man has a receding hair line. The treatment was continued on a daily basis for eight days. After 8 days, new hair growth was felt and observed. No side effects were reported as a result of using the formulation.

What is claimed is:

1. A process for preparing a composition comprising the steps of obtaining an amount of water, adding to the water a mixture of potato skins and lantana leaves, heating the mixture to boiling, maintaining the boiling of the water for a time of about three minutes to about one hour, allowing the mixture to cool to ambient temperature, and filtering the cooled mixture to obtain an aqueous solution of biochemicals.

2. A process according to claim 1 wherein the amount of water is from about 200 to about 300 milliliters, wherein the amount of potato skins added to the water is from about 1 to about 50 grams, and wherein the amount of lantana leaves added to the water is from about 0.3 to about 5 grams.

3. A process according to claim 1 further comprising the steps of recovering the aqueous solution of biochemicals and maintaining the solution under conditions of refrigeration.

4. A cosmetic composition comprising an aqueous solution of containing biochemicals obtained from boiling a mixture of potato skins and lantana leaves in water.

5. A cosmetic composition prepared according to the process of claim 1.

6. A method of using an aqueous solution containing biochemicals obtained from boiling a mixture of potato skins and lantana leaves in water comprising the steps of massaging said aqueous solution onto the scalp of a person.

7. A method of using an aqueous solution containing biochemicals obtained from boiling a mixture of potato skins and lantana leaves in water comprising the steps of massaging said aqueous solution onto the scalp of a person and leaving said aqueous solution on the scalp and hair for a time of at least four hours.

8. A method according to claim 6 wherein the composition is left on the hair and scalp for at least about four hours.

9. A method according to claim 7 wherein the composition is massaged onto the hair and scalp more than once a day.

10. A method according to claim 9 wherein the composition is massaged onto the hair and scalp at least three times a day.

11. A Process of preparing a hydrophilic composition comprising the steps of boiling a mixture of lantana leaves and potato skins in water and straining the mixture through cheesecloth to obtain said composition in aqueous form.

12. The process as described in claim 11 wherein the amount of water is from about 200 to about 300 milliliters, wherein the amount of potato skins added to the water is from about 1 to about 50 grams, and wherein the amount of lantana leaves added to the water is from about 0.3 to about 5 grams and the ingredients are boiled for about 1 hour.

13. A composition producing no side effects prepared according to the process of claim 11.

14. A composition prepared according to the process of claim 11.

15. A hydrophilic composition comprising the aqueous composition produced by the process of claim 11.

16. A hydrophilic composition comprising the aqueous composition produced by the process of claim 12.

17. A hydrophilic scalp massaging composition comprising the aqueous composition produced by the process of claim 11.

18. A hydrophilic dry skin treating composition comprising the aqueous composition produced by the process of claim 12, wherein the amounts of the ingredients are proportionally the same.

19. A Aqueous hydrophilic solution produced in conformity with the process of claim 11.

* * * * *